(12) United States Patent
Durig et al.

(10) Patent No.: US 8,968,456 B2
(45) Date of Patent: Mar. 3, 2015

(54) FILM COATING COMPOSITION FROM SOLID POWDER HYDROPHOBIC COMPOUNDS

(75) Inventors: Thomas Durig, Chadds Ford, PA (US); Divya Tewari, West Chester, PA (US)

(73) Assignee: Hercules Incorporated, Wilmington, DE (US)

( * ) Notice: Subject to any disclaimer, the term of this patent is extended or adjusted under 35 U.S.C. 154(b) by 233 days.

(21) Appl. No.: 12/869,272

(22) Filed: Aug. 26, 2010

(65) Prior Publication Data

US 2011/0048281 A1 Mar. 3, 2011

Related U.S. Application Data

(60) Provisional application No. 61/237,720, filed on Aug. 28, 2009.

(51) Int. Cl.
*C08L 1/08* (2006.01)
*A61K 9/28* (2006.01)
*A23G 3/34* (2006.01)

(52) U.S. Cl.
CPC ............. *A61K 9/2866* (2013.01); *A23G 3/343* (2013.01); *A23G 2200/00* (2013.01); *A23G 2200/06* (2013.01); *A61K 9/288* (2013.01)
USPC ..................................................... 106/203.1

(58) Field of Classification Search
None
See application file for complete search history.

(56) References Cited

U.S. PATENT DOCUMENTS

| 4,341,653 | A | 7/1982 | Inukai et al. |
| 5,077,053 | A | 12/1991 | Kuncewitch et al. |
| 5,885,617 | A | 3/1999 | Jordan |
| 6,410,054 | B1 | 6/2002 | Thosar et al. |
| 6,495,163 | B1 | 12/2002 | Jordan |
| 6,667,059 | B2 | 12/2003 | Sue et al. |
| 2004/0228916 | A1* | 11/2004 | Tanno et al. ............... 424/471 |

FOREIGN PATENT DOCUMENTS

| EP | 1 477 161 A1 | 11/2004 |
| JP | 2006188490 A | 7/2006 |
| WO | 2004/098713 A3 | 11/2004 |
| WO | 2006/082500 A1 | 8/2006 |
| WO | 2006/125132 A3 | 12/2006 |
| WO | 2009/040702 A3 | 4/2009 |
| WO | 2009/064429 A1 | 5/2009 |

OTHER PUBLICATIONS

International Search Report, Nov. 19, 2010.
Spect, F. et al, The Application of Shellac as an Acidic Polymer for Enteric Coating, Pharmaceutical Technology International, Inglewood, CA, US, vol. 10, No. 9, Jan. 1, 1998, pp. 20-28.

* cited by examiner

*Primary Examiner* — Melvin C Mayes
*Assistant Examiner* — Stefanie Cohen
(74) *Attorney, Agent, or Firm* — Shaorong Chen

(57) ABSTRACT

The present invention relates to a film coating composition used for film coating pharmaceutical tablets, nutritional supplements, confectionary forms and the like. The film coating composition comprises a water soluble film former such as hydroxypropylcellulose, hydroxypropylmethylcellulose, hydroxyethylcellulose, starches, modified starches and the like and one or more hydrophobic compounds, such as metal salt of higher fatty acids, higher fatty alcohol, natural wax either from vegetable, animal origin or synthetic wax. Optionally, the film coating composition may include plasticizers, colorants, such as pigments and/or flow aids.

14 Claims, No Drawings

FILM COATING COMPOSITION FROM SOLID POWDER HYDROPHOBIC COMPOUNDS

RELATED APPLICATIONS

This application claims the benefit of U.S. Provisional Application Ser. No. 61/237,720, filed on Aug. 28, 2009, the contents of which are incorporated herein by reference in its entirety.

FIELD OF THE INVENTION

The present invention relates to a film coating composition used for film coating pharmaceutical tablets, nutritional supplements, confectionary forms and the like. The film coating composition comprises a water soluble film former such as hydroxypropylcellulose, hydroxypropylmethylcellulose, hydroxyethylcellulose, starches, modified starches and the like, one or more hydrophobic compounds in solid powder form, such as natural wax either from vegetable or animal origin or synthetic wax. Optionally, the film coating composition may include plasticizers, pigments and/or flow aids.

BACKGROUND OF THE INVENTION

Three characteristics of pharmaceutical formulations are: physical, such as size, hardness, friability, disintegration and dissolution; chemical, such as drug content and stability and sensory, such as appearance, odor and taste. All of the three characteristics are equally important with respect to patient acceptance, preference and compliance. For example, an unpleasant odor in a formulation reduces patient acceptance, preference and compliance. Film coating is a well known art. Pharmaceutical solid dosage forms such as tablets, granules, pellets etc are film coated to protect these solid dosage forms from oxidation due to atmospheric oxygen permeation, moisture, heat, light, etc as well as to mask the odor of the pharmaceutical preparations.

Many nutraceutical and some pharmaceutical preparations are associated with unpleasant odor and taste and are susceptible to moisture or oxygen induced changes. Examples of such nutraceutical preparations are valerian root extract, garlic and many multivitamin preparations etc. Conventional approaches for masking odors of pharmaceuticals utilize sugar coating technology. Sugar coating requires non perforated coating pan, long processing times and experienced personnel to obtain products of acceptable quality, i.e., odor masking. This coating process produces tablets which are nearly double the weight of the starting core. Due to the problems associated with sugar coating technology, film coating has gained importance. There are various other methods to mask odors. One way is to add flavors to the formulation to change the taste. The goal is to make the formulation more acceptable and to increase the consumer compliance with the dosage regimen.

Protection of dosage form from environmental moisture is important when the drug is adversely affected by its presence. Common approach used to limit the degradation is to package the moisture sensitive dosage forms, such as tablets, capsules etc using specialized packaging. In places where climate is very humid the special packaging does not provide the complete moisture protection. Another way to reduce the need for special packaging is to coat the solid dosage forms with materials which reduce the moisture uptake. Moreover, these coatings should not affect the disintegration times. Examples of moisture sensitive drugs are ranitidine, temazepam, most vitamins and numerous herbals. Examples of moisture induced changes can range from degradation of drug by hydrolysis or changes in the appearance of the dosage form on storage to changes in the disintegration and dissolution times of the dosage form. Moisture barrier coatings are thus applied to augment or eliminate the need for special packaging. It protects the dosage form from degradation.

In order to achieve a moisture barrier coating, usually hydrophobic or lipophilic substances are combined with water soluble or water insoluble film forming polymer and pigments. The hydrophobic or lipophilic substances may be a polymer where the polymers generally employed for this purpose are shellac, cellulose acetate phthalate (CAP), ethylcellulose (EC) and the like. However, when coating with these polymers, use of organic solvent is typically required which also necessitates the added expense for air conditioning equipment, anti-explosion provisions, and the like to safely handle such materials. Another disadvantage of the use of these polymers is the prolonged disintegration of the dosage form in the body when ingested due to the reduced aqueous solubility of coatings made from polymers which rely upon organic solvents to process these materials into coatings.

U.S. Pat. Nos. 6,495,163 and 5,885,617 each disclose a moisture barrier film coating composition comprising polyvinyl alcohol (PVA), soya lecithin, flow aid, colorant and suspending agent. These coatings use medium viscosity grades of PVA which dissolve readily in cold water and still maintain moisture barrier properties. However, it is well known that PVA is extremely tacky and application of coatings based on PVA requires slower spray rates, higher atomization pressures and higher bed temperatures during a film coating process. This is disadvantageous to the dosage manufacturer as it doubles the coating time for a solid dosage form and thus increases the overall cost of the process used to produce coated solid dosage forms. Moreover, coatings utilizing PVA do not mask unpleasant odors produced by active ingredients.

U.S. Pat. No. 4,341,653 discloses a protective coating composition comprising a metal salt of higher fatty acid, a higher fatty acid and a wax in an aqueous solution of a water soluble film base and a surface active agent. However, this coating was produced as an emulsion which has an additional homogenization step. Also, the coatings taught in this patent are designed to delay the dissolution time to mask the taste of the active in addition to providing moisture barrier.

JP2006188490A teaches a film coating composition with improved adhesiveness, excellent coating properties which masks the smell and provides oxygen barrier. This coating comprises a polyvinylalcohol and talc and does not provide barrier to moisture.

U.S. Pat. No. 5,077,053 teaches use of Zein as a moisture barrier for sugarless edible compositions. In this composition, a two layered coating is required. The first layer being a layer of Zein and a second lay being a sugarless layer.

U.S. Pat. No. 6,667,059B2 teaches a multilayer odor barrier coating, particularly for use in valerian root tablets. In this composition, the first two layers are composed of hydroxyalkyl cellulose followed by third layer of methacrylate. Besides being time consuming to produce, this coating is not acceptable for nutraceutical uses as methacrylates are not acceptable for food use.

The disadvantages associated with above mentioned coating approaches are that the coatings are either difficult or time consuming to apply, which makes the process less cost effective, or they increase the disintegration time of the coated solid dosage form upon ingestion.

In summary, a need exists for a multifunctional barrier coating which provides moisture, odor as well as taste barrier for various nutraceutical and pharmaceutical solid preparations. There is also a need for a multifunctional barrier coating that is easy to produce from a powder and easy to apply to the solid dosage form.

BRIEF DESCRIPTION OF THE INVENTION

The present invention relates to a formulation in powder form useful for producing a sprayable dispersion useful in coating solid dosage forms. The formulation in powder form comprises a water soluble film former, a solid powder hydrophobic compound, and optionally a plasticizer. The formulation in powder form useful for producing a sprayable dispersion coating can be readily dispersed in water, without the need of high shear mixers such as homogenizers and the like to produce coatings on various substrates.

The present invention also relates to a process for producing a solid dosage form having a coating and the resultant film coated nutraceutical or pharmaceutical wherein the above described sprayable dispersion coating is sprayed as sprayable dispersion onto a nutraceutical or pharmaceutical active ingredient in a solid dosage form to produce a film coating on the nutraceutical or pharmaceutical active ingredient in a solid dosage form.

DETAILED DESCRIPTION OF THE INVENTION

It has been found that that use of one or more solid powder hydrophobic compounds, such as micronized wax, with a water soluble film former and water, results in a remarkable increase in the barrier properties of the resulting film coating. Preferably, the film coating also includes pigments and plasticizers.

The water soluble film former may be any water soluble polymer such as hydroxypropylcellulose, hydroxypropylmethylcellulose, methylcellulose, hydroxyl ethylcellulose, sodium carboxymethylcellulose, polyvinyl alcohol, copovidone, alginic acid, starch and starch derivatives, modified starch, guar and guar derivatives. The amount of water soluble film former present in the formulation in powder form useful for producing a sprayable dispersion coating ranges from about 5 to 85% by weight, more preferably from about 10 to 75% by weight, still more preferably from about 30 to 70% by weight of the total formulation in powder form.

The solid powder hydrophobic compound may be a metal salt of higher fatty acid. These metal salts would include derivatives of sodium, calcium, magnesium, zinc and aluminum in fine powder form. The preferred metal salt of higher fatty acid being magnesium stearate. The solid powder hydrophobic compound may be a higher fatty alcohol, such as lauryl, myristyl, cetyl, stearyl and the like, and having a melting point in the range of about 50-70° C. and a particle size, $d_v90$, in the range of about 10 μm-400 μm.

The solid powder hydrophobic compound may be preferably a micronized powder of wax, derived from either vegetable source such as candedilla, carnauba, jojoba, or animal source such as bees, whale, or non-natural waxes such as microcrystalline, paraffin and like, having a melting point at a range of about 55 to 90° C. and a particle size, $d_v90$, in the range of about 10 μm to 400 μm. The more preferred wax is beeswax that has been produced in a micronized powder form through the use of cryogenic milling.

The amount of solid powder hydrophobic compound present in the formulation in powder form useful for producing a sprayable dispersion coating ranges from about 5 to 50% by weight, more preferably from about 10 to 40% by weight, still more preferably from about 15 to 30% by weight of the total formulation in powder form.

The film coating may also contain a plasticizer such as triacetin, glycerin, mineral oil, acetylated monoglyceride, medium chain triglycerides, polysorbate and the like. Medium chain triglycerides are high-chain (6 to 12 carbons) fatty acid esters of glycerol.

The film coating may also optionally contain a colorant, such as a pigment. The colorant may be any food approved color, pigment, opacifier or dye. It can be aluminum lake, iron oxide, titanium dioxide or natural colors.

A dry powder composition is made to form a barrier film coating, such as moisture, oxygen, odor and taste, for pharmaceutical tablets and the like, which comprises one or more water soluble film former base, one or more of the following one or more solid powder hydrophobic compounds such as, micronized wax, metal salts of higher fatty acids and higher fatty alcohol and optionally in combination with one or more of following components such as, plasticizers, pigments and flow aids. The powder may also comprise other components such as natural or artificial sweeteners and flavors.

For the purposes of this application, the term "micronized" shall mean a material in solid form having a particle size, $d_v90$, in the range of about 10 μm-400 μm.

A method of making the dry powder composition of the invention comprises the steps of mixing one or more water soluble film former, one or more of the following solid powder hydrophobic compounds such as metal salt of higher fatty acids, higher fatty alcohol, micronized wax, and optionally plasticizer, colorant and flow aids until a homogeneous powder mixture is produced. One advantage of the dry powder composition is that it is readily water dispersible and ready to use within about 45 minutes after adding to water and stirring.

The invention is also directed to a liquid coating dispersion for forming a barrier film coating which comprises one or more water soluble polymer, one or more of the following solid powder hydrophobic compounds such as metal salt of higher fatty acid, higher fatty alcohol, micronized wax, and optionally plasticizer and/or colorant.

The method of making the liquid coating dispersion of the invention comprises dispersing the dry powder composition, or the individual ingredients of the dry powder composition separately, into water, either at ambient temperature or at slightly elevated temperature, e.g. below the melting point of the solid powder hydrophobic compounds and stirring until a homogeneous dispersion of is produced.

The moisture permeability of products with and without the barrier film coating were measured gravimetrically following exposure to 75% relative humidity (RH) at 25° C. for a period of 24 hours.

The 24 hour moisture uptake of the uncoated copper sulfate tablets was 7% and the moisture uptake of the coated tablets ranged from 1%-3.5% depending on the coating formulation.

Viscosities of the dispersions were determined using a Brookfield LTV viscometer with a #2 spindle and at 30 rpm, unless noted otherwise. The viscosities of the dispersions of the invention range from 100 cps-400 cps based on their composition.

The examples are presented to illustrate the invention, parts and percentages being by weight, unless otherwise indicated.

EXAMPLES

Cryogenic Process for Milling Beeswax 500 lbs of white beeswax, NF (National formulary, a USP/NF grade of beeswax was used) was ground in a cryogenic milling system. Five trials were performed changing different production parameters which could affect the particle size of the beeswax such as speeds (rpm), temperatures, and the mill gap (space between the rotor assembly and the internal wear ring). There were no screens on the mill and the particle size was achieved without sifting. The details of the trials are as follows:

TABLE 1

Process Parameters Used for Milling

| Process Parameters | Trial # 1 | Trial # 2 | Trial # 3 | Trial # 4 | Trial # 5 |
|---|---|---|---|---|---|
| Mill RPM | 6000 | 6000 | 4000 | 5000 | 5000 |
| Mill Gap | 0.025" | 0.030" | 0.030" | 0.052" | 0.052" |
| Mill Temp | −100° F. (−73.3° C.) | −100° F. (−73.3° C.) | −100° F. (−73.3° C.) | −100° F. (−73.3° C.) | 0° F. (−17.8° C.) |
| Cryo Screw Temp | −275° F. (−170.6° C.) | −275° F. (−170.6° C.) | −275° F. (−170.6° C.) | −275° F. (−170.6° C.) | −100° F. (−73.3° C.) |
| Cryo Screw RPM | 40 | 40 | 40 | 40 | 40 |
| Feed Screw RPM | 13 | 13 | 13 | 13 | 13 |

The particle size distribution thus obtained is as follows:

Particle Size Distribution Testing

Particle Size Distribution Method

Volume-based particle size distribution was measured by laser light diffraction using a Helos-Sympatec apparatus. The data is presented as volume-based cumulative distributions.

TABLE 2

| Sample # | $d_v 10$ (μm) | $d_v 16$ (μm) | $d_v 50$ (μm) | $d_v 90$ (μm) | $d_v 99$ (μm) | Mean Diameter (μm) |
|---|---|---|---|---|---|---|
| 1 | 9.70 | 12.48 | 38.03 | 358.02 | 471.57 | 121.12 |
| 2 | 8.39 | 10.80 | 30.43 | 330.68 | 515.53 | 108.94 |
| 3 | 8.50 | 10.84 | 25.61 | 74.59 | 203.37 | 37.31 |
| 4 | 7.32 | 9.40 | 21.21 | 56 | 107.73 | 27.44 |
| 5 | 10.48 | 13.11 | 28.83 | 72.18 | 150.04 | 36.78 |

Example 1

| Components | Percentages by weight |
|---|---|
| Hydroxypropylcellulose (Klucel ® ELF HPC, available from Hercules Incorporated) | 46% |
| Stearyl Alcohol | 10% |
| Titanium Dioxide | 38% |
| Talc | 5% |
| Polysorbate | 1% |
| Total | 100% |

The above listed components were mixed in a high shear mixer until a homogenous dry powder mixture was produced. The homogenous dry powder mixture was added to the vortex of well agitated water and mixed for 45 minutes until a dispersion of the powder mixture in water was produced.

The dispersion was then sprayed onto tablets using 15" (381 mm) perforated coating pan. The spraying was continued until a desired weight gain on the tablets was achieved.

For all the examples, coatings were applied to hygroscopic sample tablets (400 mg) comprising 5% croscarmellose as a hygroscopic wicking agent, 10% copper sulfate as a hygroscopic, hydrate-forming, model active and colorimetric moisture indicator and q.s. microcrystalline cellulose were compressed on Manesty® Beta press under similar conditions.

The coating conditions are as follows:

| Spray Coating Equipment: | |
|---|---|
| Pan | 15" O'Hara Coating Pan |
| Spray Guns | Schlick |
| Spray Coating Conditions: | |
| Batch Size (Kg) | 2.0 |
| Spray Rate (g/ml) | 20 |
| Atomizing Air Pressure (PSI) | 30 |
| Pattern Air Pressure (PSI) | 30 |
| Gun to Bed Distance (") | 6 |
| Air Temperature (° C.) | |
| Inlet | 60-65° C. |
| Exhaust | 45-50° C. |
| Pan Speed (RPM) | 16 |

A dry coating blend was obtained by blending all the powder in the high shear mixer for three minutes followed by addition of polysorbate and mixing for additional three minutes to form a dry coating blend. An amount of the dry coating blend made above was taken and added to the vortex of well agitated water and mixed for 45 minutes in order to make dispersion with 14-20% solids loading level. The hygroscopic sample tablets were coated in 15" O'Hara coating pan using the conditions given above.

The measurement of the moisture permeability of the coated and uncoated product was measured gravimetrically following the exposure to 75% relative humidity (RH) at 25° C.

The coated tablets thus obtained had good appearance and smooth surface.

Comparative Example 1

Instead of producing a dispersion of the powder mixture in water, this comparative example melts the solid powder hydrophobic compound, beeswax, and then uses an energy intensive homogenization step to produce an emulsion rather than a dispersion of the solid powder hydrophobic compound.

10 parts of 7.2% (w/w) aqueous solution of hydroxypropylmethylcellulose (HPMC) (Benecel® HPMC, available from Hercules Incorporated) was warmed to 70° C. on a waterbath. 3 parts by weight of white beeswax, NF was melted by heating on a water bath and the melted white beeswax was poured, keeping its temperature at about 70° C., into the HPMC solution with vigorous stirring using Silverson L4RT homogenizer. The HPMC emulsion containing the melted beeswax was cooled to room temperature and was observed as having a creamy appearance. 13 parts by weight of HPMC/melted beeswax emulsion thus obtained were mixed with 87 parts by weight of HPMC solution to prepare a coating solution. The time to produce this coating solution was in excess of three (3) hours.

Total solution of HPMC: 4000 g
To make 7.2% w/w solution, 288 g of HPMC E6 (Benecel® HPMC, available from Hercules Incorporated) was added to the vortex of 3712 g of well agitated water.
Amount of Beeswax used: 120 g
Final composition: HPMC 7% (w/w);
Beeswax: 3% (w/w); and
Water: 90% (w/w).
The resulting solution had a viscosity of 130 cps.
1200 g of coating solution prepared above was used for coating hygroscopic sample tablets up to 4% weight gain.

Example 2

The same procedure was used to produce coated tablets as was used in Example 1 except that a combination of hydroxypropylcellulose and hydroxypropylmethylcellulose was used as the water soluble film former.

| Components | Percentages by weight |
|---|---|
| Hydroxypropylcellulose (Klucel ® ELF HPC, available from Hercules Incorporated) | 31% |
| Stearyl Alcohol | 10% |
| Hydroxypropylmethylcellulose (Benecel ® E15 HPMC, available from Hercules Incorporated) | 15% |
| Titanium Dioxide | 38% |
| Talc | 5% |
| Polysorbate | 1% |
| Total | 100% |

The coated tablets thus obtained had good appearance and smooth surface.

Example 3

The same procedure was used to produce coated tablets as was used in Example 1 except that magnesium stearate was used as the solid powder hydrophobic compound.

| Components | Percentages by weight |
|---|---|
| Hydroxypropylcellulose (Klucel ® ELF HPC, available from Hercules Incorporated) | 46% |
| Magnesium Stearate | 10% |
| Titanium Dioxide | 38% |
| Talc | 5% |
| Polysorbate | 1% |
| Total | 100% |

The coated tablets thus obtained had good appearance and smooth surface.

Example 4

The same procedure was used to produce coated tablets as was used in Example 1 except that a combination of stearyl alcohol and Beeswax was used as the solid powder hydrophobic compound.

| Components | Percentages by weight |
|---|---|
| Hydroxypropylcellulose (Klucel ® ELF HPC, available from Hercules Incorporated) | 41% |
| Hydroxypropylmethylcellulose (Benecel ® E15 HPMC, available from Hercules Incorporated) | 5% |
| Stearyl Alcohol | 10% |
| Titanium Dioxide | 32% |
| Beeswax (obtained from Koster Keunen) | 6% |
| Talc | 5% |
| Polysorbate | 1% |
| Total | 100% |

The coated tablets thus obtained had good appearance and smooth surface.

Example 5

The same procedure was used to produce coated tablets as was used in Example 1 except that a Beeswax was used as the solid powder hydrophobic compound.

| Components | Percentages by weight |
|---|---|
| Hydroxypropylcellulose (Klucel ® ELF HPC, available from Hercules Incorporated) | 39% |
| Hydroxypropylmethylcellulose (Benecel ® E15 HPMC, available from Hercules Incorporated) | 5% |
| Titanium Dioxide | 30% |
| Talc | 5% |
| Beeswax | 20% |
| Polysorbate | 1% |
| Total | 100% |

The coated tablets thus obtained had good appearance and smooth surface.

Example 6

The same procedure was used to produce coated tablets as was used in Example 1

| Components | Percentages by weight |
|---|---|
| Hydroxypropylcellulose (Klucel ® ELF HPC, available from Hercules Incorporated) | 39% |
| Hydroxypropylmethylcellulose (Benecel ® E15 HPMC, available from Hercules Incorporated) | 5% |
| Titanium Dioxide | 35% |
| Talc | 5% |
| Beeswax | 15% |
| Polysorbate | 1% |
| Total | 100% |

The coated tablets thus obtained had good appearance and smooth surface.

Example 7

The same procedure was used to produce coated tablets as was used in Example 1 except that Beeswax was used as the solid powder hydrophobic compound, and that triacetin was used as a plasticizer.

| Components | Percentages by weight |
|---|---|
| Hydroxypropylmethylcellulose (Benecel ® E6 HPMC, available from Hercules Incorporated) | 36% |
| Hydroxypropylmethylcellulose (Benecel ® E15 HPMC, available from Hercules Incorporated) | 5% |
| Triacetin (obtained from Univar) | 10% |
| Titanium Dioxide | 30% |
| Talc | 4% |
| Beeswax | 15% |
| Total | 100% |

The coated tablets thus obtained had good appearance and smooth surface.

Example 8

The same procedure was used to produce coated tablets as was used in Example 7 except that a greater amount of the beeswax was used as the solid powder hydrophobic compound, and that triacetin was used as a plasticizer.

| Components | Percentages by weight |
|---|---|
| Hydroxypropylmethylcellulose (Benecel ® E6 HPMC, available from Hercules Incorporated) | 32% |
| Hydroxypropylmethylcellulose (Benecel ® E15 HPMC, available from Hercules Incorporated) | 4% |
| Triacetin (obtained from Univar) | 10% |
| Titanium Dioxide | 30% |
| Talc | 4% |
| Beeswax | 20% |
| Total | 100% |

The coated tablets thus obtained had good appearance and smooth surface.

Example 9

The same procedure was used to produce coated tablets as was used in Example 7 except that no talc was added to the composition.

| Components | Percentages by weight |
|---|---|
| Hydroxypropylmethylcellulose (Benecel ® E6 HPMC, available from Hercules Incorporated) | 32% |
| Hydroxypropylmethylcellulose (Benecel ® E15 HPMC, available from Hercules Incorporated) | 4% |
| Triacetin (obtained from Univar) | 10% |
| Titanium Dioxide | 34% |
| Beeswax | 20% |
| Total | 100% |

The coated tablets thus obtained had good appearance and smooth surface.

Example 10

The same procedure was used to produce coated tablets as was used in Example 9.

| Components | Percentages by weight |
|---|---|
| Hydroxypropylmethylcellulose (Benecel ® E6 HPMC, available from Hercules Incorporated) | 32% |
| Hydroxypropylmethylcellulose (Benecel ® E15 HPMC, available from Hercules Incorporated) | 4% |
| Glycerin | 9% |
| Medium Chain Triglycerides | 3% |
| Titanium Dioxide | 34% |
| Beeswax | 20% |
| Total | 100% |

The coated tablets thus obtained had good appearance and smooth surface.

Example 11

The same procedure was used to produce coated tablets as was used in Example 9 except that FD&C Yellow #6 and D&C Yellow colors were added to the composition.

| Components | Percentages by weight |
|---|---|
| Hydroxypropylmethylcellulose (Benecel ® E6 HPMC, available from Hercules Incorporated) | 28.6% |
| Hydroxypropylmethylcellulose (Benecel ® E15 HPMC, available from Hercules Incorporated) | 3.6% |
| Triacetin | 10% |
| Titanium Dioxide | 30% |
| Beeswax | 20% |
| FD&C Yellow # 6 | 0.2% |
| D&C Yellow # 10 | 7.6% |
| Total | 100% |

The coated tablets thus obtained had good appearance and smooth surface.

Example 12

The same procedure was used to produce coated tablets as was used in Example 9 except that no titanium dioxide was added to the composition.

| Components | Percentages by weight |
|---|---|
| Hydroxypropylmethylcellulose (Benecel ® E6 HPMC, available from Hercules Incorporated) | 62.2% |
| Hydroxypropylmethylcellulose (Benecel ® E15 HPMC, available from Hercules Incorporated) | 7.8% |
| Triacetin | 10% |
| Beeswax | 20% |
| Total | 100% |

The coated tablets thus obtained had good appearance and smooth surface.

While the invention has been described with respect to specific embodiments, it should be understood that the invention should not be limited thereto and that many variations and modifications are possible without departing from the spirit and scope of the invention.

What is claimed is:

1. A powder composition, comprising:
   i. a water soluble film former, and
   ii. a solid hydrophobic powder,
   wherein the solid hydrophobic powder comprises particles having a size distribution where $d_v$ 90 is in a range of from 56 μm to 400 μm.

2. The powder composition of claim 1, wherein the water soluble film former is selected from the group consisting of hydroxypropylcellulose, hydroxypropylmethylcellulose, methylcellulose, hydroxyl ethylcellulose, sodium carboxymethylcellulose, polyvinyl alcohol, copovidone, alginic acid, starch and starch derivatives, modified starch, guar, and guar derivatives.

3. The powder composition of claim 2, wherein the water soluble film former comprises hydroxypropylcellulose.

4. The powder composition of claim 2, wherein the water soluble film former comprises hydroxypropylmethylcellulose.

5. The powder composition of claim 1, wherein the solid hydrophobic powder comprises a higher fatty alcohol selected from the group consisting of lauryl, myristyl, cetyl and stearyl alcohols.

6. The powder composition of claim 1, wherein the solid hydrophobic powder has a melting point in a range of from about 55 to 90° C. and comprises a micronized powder of wax derived from a vegetable source, an animal source, or a non-natural wax.

7. The powder composition of claim 6, wherein the solid hydrophobic powder comprises a micronized powder of wax derived from an animal source selected from the group consisting of bees and whales.

8. The powder composition of claim 7, wherein the micronized powder of wax is beeswax.

9. The powder composition of claim 1, further comprising a plasticizer.

10. The powder composition of claim 9, wherein the plasticizer is selected from the group consisting of triacetin, glycerin, mineral oil, acetylated monoglyceride, medium chain triglycerides, and polysorbate.

11. The powder composition of claim 1, further comprising a colorant selected from the group consisting of any food approved color, pigment, opacifier, and dye.

12. The powder composition of claim 11, wherein the pigment is selected from the group consisting of aluminum lake, iron oxide, and titanium dioxide.

13. The powder composition of claim 1,
   wherein the solid hydrophobic powder comprises particles having a size distribution where $d_v$ 90 is in a range of from 56 μm to 358 μm.

14. The powder composition of claim 1,
   wherein the solid hydrophobic powder comprises particles having a size distribution where $d_v$ 50 is in a range of from 21 μm to 38 μm.

* * * * *